United States Patent [19]

Hill-Byrne

[11] Patent Number: 4,727,865

[45] Date of Patent: Mar. 1, 1988

[54] REPLACEABLE RIGID CAST WITH INTEGRAL FASTENERS

[76] Inventor: Christopher R. Hill-Byrne, 2690 Drew St., Apt. 861, Clearwater, Fla. 33519

[21] Appl. No.: 709,184

[22] Filed: Mar. 7, 1985

[51] Int. Cl.⁴ .................................................. A61F 5/04
[52] U.S. Cl. .................................. 128/89 R; 24/68 SK
[58] Field of Search ............... 128/90, 91 R, 83, 83.5, 128/88, 87 R, 89 R; 36/50; 264/222; 24/68 SK

[56] References Cited

U.S. PATENT DOCUMENTS

| | | | |
|---|---|---|---|
| 101,743 | 4/1870 | King | 128/89 R |
| 2,103,942 | 12/1937 | Gillin | 128/91 R |
| 2,506,254 | 5/1950 | Toreson | 128/133 X |
| 2,761,443 | 9/1956 | Parker | 128/91 R |
| 3,032,033 | 5/1962 | Ramirez | 128/90 |
| 3,085,569 | 4/1963 | Cook | 128/83.5 X |
| 3,580,248 | 5/1971 | Larson | 128/89 R |
| 3,643,656 | 2/1972 | Young | 128/90 |
| 3,680,548 | 8/1972 | Brown | 128/90 |
| 4,051,611 | 10/1977 | Chalmers | 36/50 |
| 4,129,127 | 12/1978 | Ellison | 128/91 R |
| 4,465,064 | 8/1984 | Boone | 128/88 |
| 4,510,888 | 4/1985 | DeAngelis | 128/88 |

OTHER PUBLICATIONS

Nicholas et al., Arch. Phys. Med. Rehabil., vol. 53, pp. 264–267 (Jun. 1977).
Nicholas et al., Arch. Phys. Med. Rehabil., vol. 63, pp. 95–96 (Feb. 1982).

Primary Examiner—Richard J. Johnson
Attorney, Agent, or Firm—Birch, Stewart, Kolasch & Birch

[57] ABSTRACT

A rigid cast which is useful for immobilizing injured body parts, which is essentially removable and subsequently replaceable after removing same, comprising a rigid structure of two or more integral components, which at least partially surround said injured body parts, consisting of: (1) at least one material, which is shaped to conform to the contour of said body parts; and (2) at least one cooperating fastener means which is effective in securing said material allowing the resultant components to achieve said immobilization of said body parts.

9 Claims, 4 Drawing Figures

REPLACEABLE RIGID CAST WITH INTEGRAL FASTENERS

BACKGROUND OF THE INVENTION

1. Field of the Invention

This invention relates to devices useful for immobilizing parts of the body. More particularly, the present invention relates to a rigid cast which may be removed and subsequently replaced, useful for immobilizing or compressing parts of the body, and which conforms to the shape of said body parts, and which also overcomes obstacles present with the use of rigid casts which, subsequent to removal, are not replaceable.

2. Description of the Prior Art

Rigid casts and the like of the type used to prevent the mobility of, or to apply desired compression to, injured or otherwise damaged parts of the body, or combinations of these, have been known and used for centuries. Such rigid devices have been applied to the injured body part in recent times in a series of steps which permit wrapping of the injured limb or other body part with a flexible bandage or the like, followed by the application of a medium, such as plaster of paris, fiberglass, etc., which subsequently hardens on the surface to produce a rigid product which effectively prevents mobility and may also apply a degree of compression to the injured part.

Rigid casts of the prior art describe a plurality of improvements thereto, however, such casts thus described, when removed for any purpose, are not reuseable on the injured limb, and must be replaced if removed by repeating the application process professionally at considerable time and expense and varying degrees of risk in attaining the original shape of the prior cast and in duplicating the degree of compression of said cast.

While supports for injured limbs are described in the prior art, such as traction bands and the like, and while these are removable and replaceable at will, such devices are not rigid and do not generally supply the required support for the proper healing of broken or more severely damaged parts of the body. U.S. Pat. No. 3,867,930 to Brown describes a necessarily flexible and removable traction band of this type with such limited use, which is fabricated from a multi-ply fabric supplying the required tension. U.S. Pat. No. 1,980,486 to King et al. describes a device secured to the patient's foot with straps, however, the teachings set forth therein offer no substantial means of support to a broken or more severely damaged limb. U.S. Pat. No. 2,875,752 to Lovich describes an improvement relating to a foot support for a rigid, though not removeable and replaceable, cast, having similar function to that of Silverman in U.S. Pat. No. 3,584,402. Of the prior art references available, none are found to overcome the burdens of removing and easily replacing a rigid cast which has been molded specifically to conform to the contour of an injured body part.

SUMMARY OF THE INVENTION

It is a principal object of the present invention to provide an improved rigid cast which is both easily removable and easily replaceable.

It is a second object of the present invention to provide an improved rigid cast which allows for the control or adjustment of the compression of desired areas of injured body parts.

It is a third object of the present invention to provide a means of removing and replacing a rigid cast with minimal discomfort to the patient wearing same, and in a fraction of the time heretofore required for such as procedure.

It is a fourth object of the present invention to provide an expedient means of removing a rigid cast from a patient in the event of a medical emergency, and a facile and expedient means of replacement thereof as may be desired.

It is a fifth object of the present invention to overcome the obstacles and undesirable circumstances associated with rigid casts due to not being able to quickly and easily remove and replace same.

It is a sixth object of the present invention to provide a more economical and less costly means of allowing the removal and replacement of a rigid cast.

it is a seventh object of the present invention to provide an effective means of preventing discomfort and medical complications due to microbial growth and other complications.

In the broadest aspects, the present invention is directed to a rigid cast useful for immobilizing an injured part, which is removable and subsequently replaceable after removal, and having rigid body part immobilizing parts adapted to at least partially surround an injured body part. Preferably, at least one material may be shaped to conform to the contour of said body part, said material being affixed with cooperating fasteners for securing said rigid parts, thereby allowing the resultant components to achieve immobilization of said body part.

In a preferred embodiment, the cast of the present invention is formed by first encasing an injured body part in a soft material and subsequently applying a suitable casting medium over said soft material. Once said casting material becomes rigid, the formed rigid shell is cut to allow removal thereof. After said removal of said rigid shell, the cooperating fasteners are affixed to parts of same, and said rigid shell is subsequently replaced on said injured body part and secured with said fasteners.

DETAILED DESCRIPTION OF THE INVENTION

Figure 1:
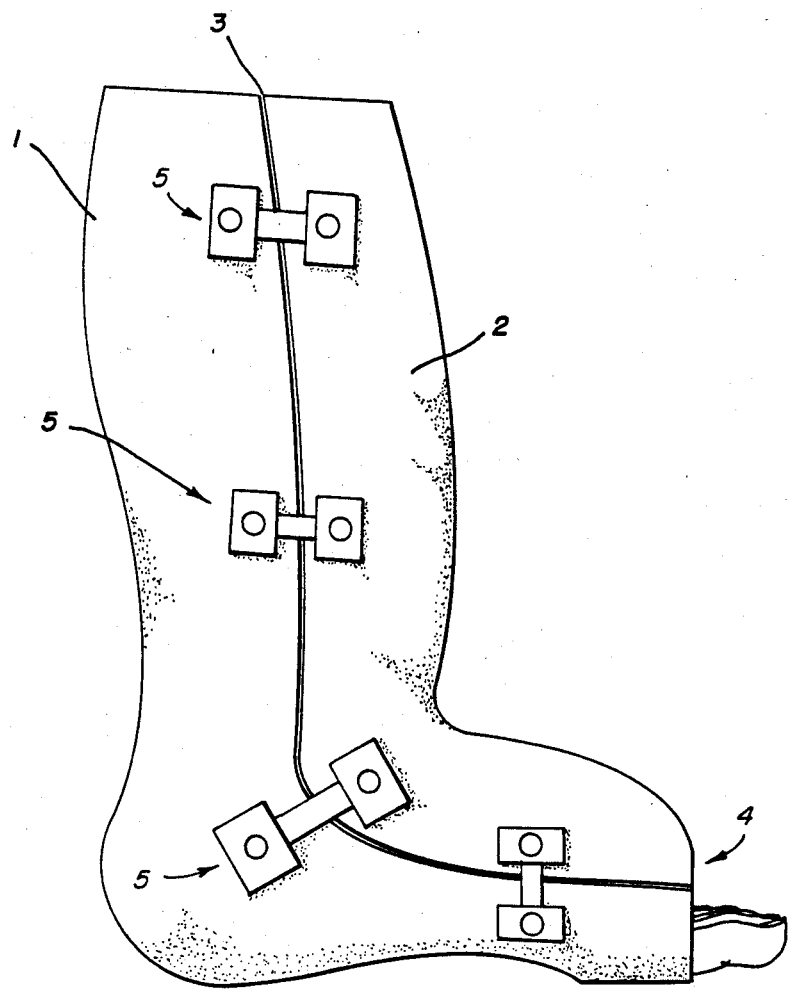
FIG. 1 is a perspective view of a preferred embodiment of the present invention shown in position on the foot of a patient.

In a preferred embodiment of the present invention, referring now to the drawings wherein like reference numerals refer to like and corresponding parts in the several views therein, an ankle cast may be formed of a back rigid part 1 and a front rigid part 2. The cast of the present invention may extend longitudinally or transversely about an injured limb or the like. Said parts, when attached by the methods more fully set forth herein along adjacent edges or cut line 3, comprise the rigid structure of the present invention. The complete structure may optionally have an open tow section 4 or may contain other openings such as holes and the like as desired to allow for additional comfort, ventilation, observation, and the like.

The rigid parts 1 and 2 may be constructed of any material known in the art to be used to produce such a rigid support, such as plaster of paris, fiberglass or other resins, plastic materials that are caused to polymerize through catalytic action subsequent to application, and similar materials. In addition thereto, said materials may consist of other rigid substances which may be preformed prior to, or during, fitting of the final cast of the present invention, such as aluminum or other metals, fiberglass, rigid plastic materials, plaster, wood, or any rigid material useful in the art for the immobilization of injured parts of the body and the like.

A plurality of integral fasteners 5 are mounted on parts 1 and 2 along the adjacent edge 3, preferably on the exterior surface, but not limited thereto, thereby securing parts 1 and 2 as a rigid structure. Preferably, such fasteners may be adjustable to allow variable degrees of rigid support of a part of the body as required. Any fasteners known in the art to be easily fastened and removed one or more times, which may produce a tension between parts 1 and 2 leading to subsequent support of an injured body part and the like may be used to secure 1 and 2. Fastener 5, as more fully detailed in FIG. 2, and illustrating in part a preferred embodiment of the present invention, represents a fastener generally useful for this purpose. Other fasteners are also useful, such as taught in U.S. Pat. No. 2,717,437 to de Mestral, removable adhesive devices, elastic materials, fasteners using springs, inelastic materials such as rope, wire, etc., and the like.

The integral fasteners are preferably used between opposing sides 1 and 2 across opposing edges 3 of the cast of the present invention, but may also be placed at any position thereon for convenience, stability, or other reasonable purposes. While at least one fastener or set thereof is required to carry out the purposes of the present invention, additional of said fasteners may be optionally replaced by hinges or other devices which simplify removal and replacement of parts 1 and 2 of the cast of the invention by allowing parts thereof to remain connected together in order to further facilitate removal and replacement of the cast of the invention and allow improved rigidity and other attributes thereof.

Figure 2:
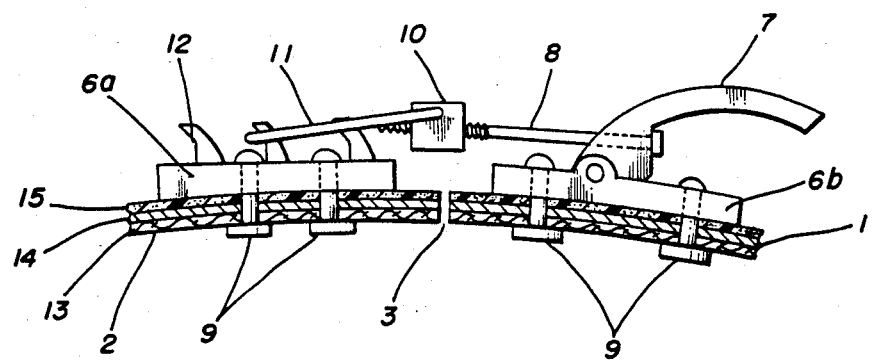
FIG. 2 is a side view of a detailed integral fastener in a preferred embodiment of the invention, mounted on the rigid cast of the invention.
Figure 3:
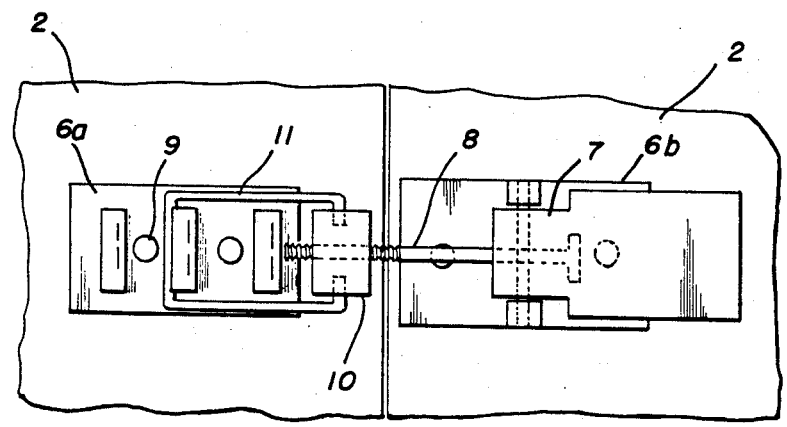
FIG. 3 is an alternate view of the fastener illustrated in FIG. 2.

An example of one integral fastener useful in the present invention is illustrated in FIG. 2, and comprises a fastener having at least two base portions, at least one of each said portions being attached to sections 1 and 2 across cut line 3. One base portion 6a, is preferably stationary when mounted to either section and is secured by one or more connectors 9 useful for such purposes. The use of two or more said connectors is preferred in cases in which the rotation or movement of base portion 6a is undesirable. The complementary parts, base portion 6b, lever 7, screw 8, screw block 10, and fastening loop 11 are preferably mounted opposite base portion 6a, and in a similar manner to base portion 6a, and are preferably movable once attached to allow the application and removal of tension between rigid parts 1 and 2. Adjustment of tension may be accomplished by pressing down lever 7 to alter the distance between parts 6a and 6b, preferably by changing the position of lever 7 with respect to the rigid surface of the cast. The fastener preferably contains at least one adjustment mechanism, such as parts screw 8 and screw block 10, to allow for changes in the circumference or degree of tension between parts 1 and 2 of the cast of the invention, said adjustment being made through altering the distance between lever 7 and screw block 10 preferably by rotating screw block 10 about screw 8. In a more preferred embodiment of the present invention, said adjustment may serve as a fine adjustment, with the initial adjustment made through the connection of loop 11 with one of the projections 12 which allows for the selection of discrete distance intervals between parts 1 and 2 by varying the width of the cut line 3.

The fastener of FIG. 2 is attached to parts 1 and 2 by connectors 9, which is also a fastener device useful to attach objects to a rigid surface, such as rivets, screws, bolts, and the like, and is preferably a device which is easily and quickly attached to minimize the cost of the cast of the invention through the ease of said attachment thereto. Connector 9 consists of one or more parts which may be fabricated from materials known in the art, such as aluminum, steel, brass or other metals or alloys thereof, suitable plastic materials, including, but not limited to, synthetic materials such as polystyrene, polyethylene, polypropylene, urethanes and other polymers, fiberglass and other resins, hard rubber, wood, and the like.

The entire fastener of FIG. 2 may be made of any known material in the art useful for such purpose to carry out the objects of the present invention, such as steel, copper, brass, aluminum or other metals or alloys, rigid plastic or other synthetic materials known in the art, wood, and the like, or combinations thereof.

Figure 4:
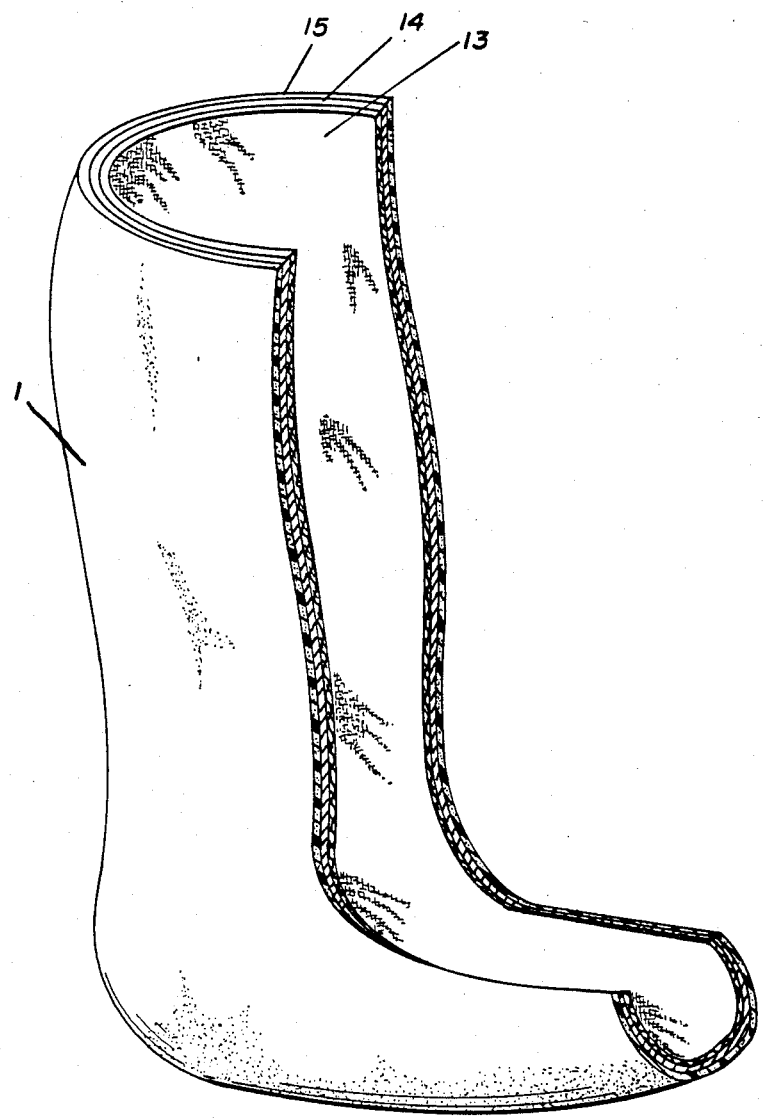
FIG. 4 is a side view of the cast shown in FIG. 1 with a portion of said cast removed for clarity, showing the interior of same.

FIG. 4 illustrates a side view of a preferred embodiment of the cast of the present invention with front 2 removed to show the interior thereof. In carrying out a preferred embodiment of the application of the present invention, (1) the injured body part may be covered with a flexible, elastic material 13 as widely practiced in the art, such as a cast stocking or the like; (2) said body part may be wrapped in any suitable cushioning material 14, known in the art, or optionally any flexible cushioning material, or combinations thereof, to further minimize contact between said body part and the cast; (3) said body part may be covered in an additional layer 15 of flexible elastic material, such as a cast stocking or the like, or other suitable material such as flexible polymeric material known in the art for minimizing adhesion of the rigid cast material to said cushioning material, or preferably said body part may be covered in a singular material comprising a combination of the methods and materials set forth herein as used in 13, 14, and 15; (4) the casting medium is applied to form a rigid shell using known methods; (5) the rigid portion of the cast as decribed above is cut and removed from the body part in two or more parts through the use of techniques common to the art; (6) the fasteners described as preferred embodiments herein are attached to rigid portions of the cast after removal as described herein, or optionally, said fasteners may be incorporated into the cast during the formation of the rigid portion thereof, or optionally combinations of the methods of fastener attachment to said rigid portions may be employed; and (7) the completed cast of the invention is replaced and secured with fasteners as herein described, which optionally may include locks to prevent removal in appropriate circumstances, such as when the cast of the invention is used with children or in veterinary use, on said body part, thus completing the preferred process of application. Such preferred embodiment as set forth herein is useful for human and veterinary use and for other variations set forth in this specification within the spirit and scope of the present invention as set forth herein.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A rigid cast which is useful for immobilizing an injured body part, which is readily removable and subsequently replaceable after removal by a user, comprising:
    two rigid body part immobilizing parts adapted to surround and conform exactly to an injured body part, said rigid body part immobilizing parts having been custom formed by applying a casting medium to said body part so that said casting medium conforms exactly to said body part, allowing said casting medium to harden on said body part to form a unitary rigid supporting shell, making two longitudinal cuts in said unitary rigid supporting shell to form said two rigid body part immobilizing parts which each have opposing and cooperating cut faces along each of said two cuts and integrally attaching a plurality of cooperating releasable fastener means to each of said rigid body part immobilizing parts on opposite sides of at least one of said longitudinal cuts for releasably and replaceably securing said rigid body part immobilizing parts along said cooperating cut faces, said cooperating releasable fastener means being capable of mechanically compressing said two rigid body part immobilizing parts onto said injured body part; and
    at least one soft inner material located on the interior of said cast which is shaped to conform exactly to the contour of said body parts thereby allowing said rigid body part immobilizing parts to achieve immobilization and compression of said body part.

2. The rigid cast of claim 1, wherein comprises a plurality of said fastener means along said at least one of said longitudinal cuts and hinge means provided along the other of said longitudinal cuts.

3. The rigid cast of claim 1, wherein said fastener means is adjustable and can be preset for a desired degree of compression.

4. The rigid cast of claim 1, wherein said cooperating releasable fastener means comprises loop means attached to one of said rigid body part immobilizing parts adjacent to said at least one of said longitudinal cuts for providing an opening and projection means attached to said other rigid body part immobilizing part for insertion into said opening, wherein said loop means and said projection means cooperate to effectuate said compression.

5. The rigid cast of claim 4, wherein said fastener means further comprises a lever for effectuating said compression.

6. The rigid cast of claim 1, which is adapted to conform to a lower leg and ankle of said user.

7. The rigid cast of claim 1, which is made out of fiberglass.

8. The rigid cast of claim 1, which is made out of plaster of paris.

9. A method of custom forming a rigid cast which is useful for immobilizing an injured body part, which is readily removable and subsequently replaceable after removal by a user comprising the steps of:
    applying at least one soft inner material onto said injured body part to conform exactly to the contour of said injured body part;
    applying a casting medium to said body part so that said casting medium conforms exactly to said body part, allowing said casting medium to harden on said body part to form a unitary rigid supporting shell;
    making two longitudinal cuts in said unitary supporting shell to form two rigid body part immobilizing parts which each have opposing and cooperating cut faces along each of said two cuts; and
    integrally attaching a plurality of cooperating releasable fastener means to each of said rigid body part immobilizing parts on opposite sides of at least one of said longitudinal cuts for releasably and replaceably securing said rigid body part immobilizing parts along said cooperating cut faces, said releasable fastener means being capable of mechanically compressing said two rigid body part immobilizing parts onto said injured body part.

* * * * *